United States Patent [19]

Baldwin et al.

[11] Patent Number: 4,946,675

[45] Date of Patent: Aug. 7, 1990

[54] HEPATIC BLOCKING AGENTS

[75] Inventors: Robert W. Baldwin, Long Eaton, England; Vera S. Byers, San Francisco, Calif.

[73] Assignee: Xoma Corporation, Berkeley, Calif.

[21] Appl. No.: 55,266

[22] Filed: May 27, 1987

[51] Int. Cl.[5] ............ A61K 39/00

[52] U.S. Cl. ............ 424/85.91; 514/2; 514/8; 514/23; 514/59; 514/885; 530/389; 530/391; 435/7; 435/810; 436/543

[58] Field of Search ............ 424/85.91; 514/2, 8, 514/23, 59, 885, 85.91; 530/389, 391; 435/7, 810; 436/543

[56] References Cited

U.S. PATENT DOCUMENTS

| | | | |
|---|---|---|---|
| 4,386,026 | 5/1983 | Ponpipom et al. | 536/53 |
| 4,745,180 | 5/1988 | Moreland et al. | 514/2 |
| 4,749,566 | 6/1988 | Casellas et al. | 514/2 |
| 4,766,106 | 8/1988 | Katre et al. | 424/85 |

FOREIGN PATENT DOCUMENTS 0213881 3/1987 European Pat. Off. .

OTHER PUBLICATIONS

Byers et al., CA, vol. 118, 1987, #15719p.
Skilleter et al., *FEBS*, 196(2), 1986, pp. 344–347.
Bourrie et al., *Eur. J. Biochem.*, 155, 1986, pp. 1–10.
Site-Specific Drug Delivery, ed. Tomlinson et al., 1986, pp. 49–52.
Kartner et al., *Scientific Am.*, Mar. 1989, pp. 44–51.
Ashwell et al., *TIBS*, 1977, pp. 76–78.
Kawasaki et al., Biochem & Biophy. Res. Comm., vol. 81, 1978, pp. 1018–1024.
Stahl and Schlesinger, *TIBS*, (Jul. 1980), 194–196.
Simmons et al., *J. Med. Chem.*, (1981), 24:1388–1395.
Ponpipom et al., *J. Med. Chem.*, (1981), 24:1388–1395.
Bourrie et al., *Eur. J. Biochem.*, (1986) 155:1–10.
Skilleter and Foxwell, *FEBS Letters*, (1986), 196:344–348.
Ashwell and Morell, "The Role of Surface Carbohydrates in the Hepatic Recognition and Transport of Circulating Glyco Proteins", *Advances in Enzymology and Related Areas of Molecular Biology*, vol. 41 (A. Meister, ed.), pp. 99–128, New York: Interscience Publication, a division of John Wiley and Sons, 1974.
Shen, T., "Cell Surface Receptors", *Directed Drug Delivery, A Multidisciplinary Problem*, (R. Borchardt, A. Repta, and V. Stella (eds.), pp. 231–245, Clifton, N.J.: Humana Press, 1985.

*Primary Examiner*—Garnette Draper
*Attorney, Agent, or Firm*—Townsend and Townsend

[57] ABSTRACT

Novel methods and compositions are provided for the enhancement of the biodistribution of immunoconjugates useful in the diagnosis and treatment of a variety of conditions including cancer in many of its forms. The compositions of the present invention provide for enhanced bioavailability of immunoconjugates for the most part by blocking mammalian cell surface receptors present on cells of the reticuloendothelial system, especially in tissues responsible for the elimination of waste products and blood filtration. Such tissues include the liver, spleen, and kidneys. The compositions are administered in conjunction with an immunoconjugate in a pharmaceutically acceptable vehicle and may be provided in kits for convenient administration.

10 Claims, No Drawings

HEPATIC BLOCKING AGENTS

BACKGROUND OF THE INVENTION

1. Field of the Invention

The present invention relates generally to immunoconjugates and, more particularly, to hepatic and reticuloendothelial blocking agents useful in the enhancement of the bioavailability of therapeutic and diagnostic immunoconjugates.

The advent in 1975 of hybridoma technology and subsequent monoclonal antibody (MoAb) production spawned an entire industry devoted to the development of MoAb-based products. The property of MoAbs of greatest interest is their ability to bind antigenic determinants or epitopes of predefined specificity. This property has led the news media to describe MoAbs as "magic bullets."

Founded on the theory of employing MoAbs as targeting agents for the cell-specific delivery of therapeutic or diagnostic moieties, much of the art has been concerned with the development of compositions known as immunoconjugates. These compositions are created by forming a molecular bond between a therapeutic or diagnostic moiety and a MoAb or an active binding fragment thereof Such conjugates are useful in the diagnosis and treatment of a variety of medical conditions, not the least of which being cancer in many of its forms.

As promising as immunoconjugates appear, they nonetheless share a common problem associated with the administration of any drug to an animal or a human; the problem of bioavailability or biodistribution. That is, the drug or agent must be made available to the target cells in a useful form and in an efficacious concentration. Clinicians constantly battle with the mammalian body's remarkable ability to rapidly clear drugs via the liver, kidneys and other organs. While a variety of compositions have been tested with respect to enhancing the biodistribution of drugs such as, for example, chemotherapeutic agents, efficacy of these compositions with respect to immunoconjugates is largely unproven. There is therefore a need for methods and compositions proven useful in enhancing the biodistribution of immunoconjugates.

2. Description of the Relevant Literature

Stahl and Schlesinger, TIBS (July 1980) - :194–196, discuss recognition and clearance of certain substances terminating in mannose which have short plasma survival times mediated via receptors on Kupffer cells and macrophages.

Simmons, et al., *J. Biol. Chem.* (June 1986) 261:7912–7920, describe mannose receptor uptake of ricin and RTA by macrophages, and show that removal of carbohydrate from ricin decreases uptake and toxicity.

Ponpipom et al., *J. Med. Chem.* (1981) 24:1388–1395 describe D-mannosyl peptide analogues (including $Man_3Ly_2$) which block uptake of labeled D-mannose-bovine serum albumin by rat alveolar macrophages.

Bourrie, et al., *Eur. J. Biochem.* (1986) 155:1–10, report on rapid clearance of an immunotoxin due to recognition of RTA mannose residues by liver cells, and enhancement of levels of immunotoxin in circulation by the coadministration of yeast mannan which inhibits liver uptake.

Skilleter and Foxwell, *FEBS Letters* (1986) 196:344–348, discuss inhibition of liver cell uptake of ricin A chain using D-mannose, L-fucose or ovalbumin.

Ashwell and Morell, "The role of surface carbohydrates in the hepatic recognition and transport of circulating glyco proteins." In *Advances In Enzymology and Related Areas of Molecular Biology,* Vol. 41 (A. Meister, ed.), p. 99–128. New York: Interscience Publication, a division of John Wiley and Sons, 1974, provide an overview of hepatic recognition of circulating glycoproteins via their surface carbohydrates.

Shen. T., "Cell surface receptors." In *Directed Drug Delivery, A Multidisciplinary Problem,* (R. Borchardt, A. Repta, and V. Stella (eds.), p. 231–45. Clifton, N.J.: Humana Press, 1985, discusses the uptake of mannosyllysine via receptors on Kupffer cells.

SUMMARY OF THE INVENTION

Novel methods and compositions are provided for the enhancement of the biodistribution of immunoconjugates useful in the diagnosis and treatment of a variety of conditions including cancer in many of its forms. The compositions of the present invention provide for enhanced bioavailability of immunoconjugates for the most part by blocking mammalian cell surface receptors present on cells of the reticuloendothelial system, especially in tissues responsible for the elimination of waste products and blood filtration. Such tissues include the liver, spleen, and kidneys. The compositions are administered in conjunction with an immunoconjugate in a pharmaceutically acceptable vehicle and may be provided in kits for convenient administration.

DETAILED DESCRIPTION OF THE SPECIFIC EMBODIMENTS

According to the present invention, novel methods and compositions are provided for use in conjunction with immunoconjugates which enhance the bioavailability and biodistribution of such conjugates. It has been discovered that the biodistribution of an immunoconjugate may be enhanced by chemically blocking certain cell surface receptors within tissues responsible for the filtration of blood and the elimination of waste products. Tissues of interest include the spleen, kidneys, and liver of a mammalian host, with the liver being of particular interest.

Immunoconjugates of interest with respect to the present invention include those for diagnostic and therapeutic use and comprise an immunoglobulin, usually a monoclonal antibody, or binding fragment thereof, conjugated to a diagnostic or therapeutic moiety. Diagnostic moieties of interest include detectable labels such as paramagnetic materials, radionuclides, or the like. Therapeutic moieties of interest include radionuclides, chemotherapeutic agents, such as methotrexate or the like, toxins, ribosomal inhibiting proteins, or the like. Of particular interest are toxic lectins such as abrin or ricin or their toxic A chains, more particularly the A chain of ricin. Such agents may be conjugated with the immunoglobulin moiety by a variety of techniques well known to those skilled in the art. Of particular interest is conjugation via a covalent disulfide bond such as disclosed in U.S. Pat. No. 4,590,071, which is hereby incorporated by reference. It will be appreciated by those skilled in the art that the conjugation methodology will generally not affect the utility of the present invention.

A large number of immunoconjugates are known in the art, many of which are produced by Xoma Corporation, Berkeley, Calif. These include a number of immunotoxins employing ricin A chain or A chain subunits ($A_1$ and $A_2$) as a toxic moiety, such as immunotoxins XMMME-001-RTA, XMMME-002-RTA, XMMCO-791-RTA, XMMCO-228-RTA, XMMLY-H65-RTA, and XMMLY-4A2-RTA, all of which are employed in therapy protocols. These immunoconjugates are of particular interest due to the high affinity of ricin A chain for mannose receptors found on macrophages including those in the liver known as Kupffer cells. This affinity results in the binding of RTA in the liver and a decrease in the concentration of the immunoconjugate in the blood of the host.

According to the present invention carbohydrate compositions, glycoprotein compositions or synthetic ligands are administered to a host in conjunction with an immunoconjugate. Carbohydrates of interest include mannose and mannose containing compositions. Glycoproteins of interest include ovalbumin, ovomucoid, mannan, or the like. Mannosylated compositions, such as mannosylated human serum albumin, mannosylated bovine serum albumin, mannosylated dextran, or the like.

According to a further aspect of the invention, a synthetic ligand may be administered to a host in the same manner as the above glycoproteins. Synthetic ligands of interest include those disclosed in U.S. Pat. No. 4,386,026, which is hereby incorporated by reference, and usually are those selected from the group having the general formula:

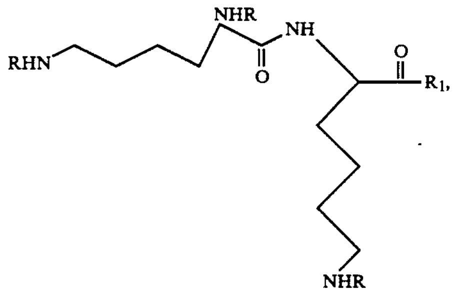

wherein R is a saccharide compound selected from the group consisting of

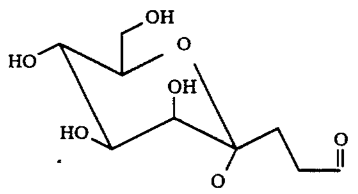

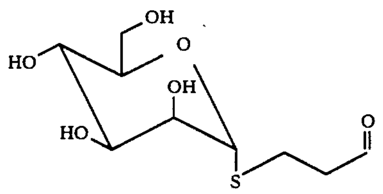

-continued

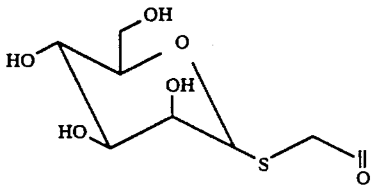

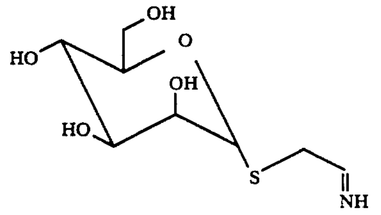

and $R_1$ is selected from the group consisting of hydroxyl and $NHR_2$ wherein $R_2$ is 6- aminohexyl and acid addition salts thereof.

Of particular interest with respect to immunoconjugates including ricin A chain as a toxic moiety are synthetic ligands which bind to oligosaccharide receptors on cells, especially those which bind to hepatic macrophages known as Kupffer cells. An example of such a compound is mannosyl$_3$lysine$_2$ ($Man_3Ly_2$) having the following formula:

$N^2$-{N2,$N^6$-Bis[3-(α-D-mannopyranosylthio)propionyl]-L-lysl}$N^6$-[3-(α-D-mannopyranosylthio)-propionyl]-L-lysine, According to the invention, the carbohydrate, glycoprotein and ligand compositions are administered to a host in a dose sufficient to enhance the biodistribution of a concurrently administered immunoconjugate. A dose range of about 0.1 mg/kg to about 1.0 g/kg, usually about 10 mg/kg to about 500 mg/kg, and particularly about 50 mg/kg to about about 250 mg/kg will result in an increase in blood concentration of immunoconjugate (measured at 10 to 30 minutes post administration) in the range of about 1.1:1 to about 10:1, usually about 1.5:1 to about 8:1 and more usually about 2:1 to about 5:1. The blocking agents are administered concomitantly with an immunoconjugate of choice; that is, shortly before, during, or shortly after immunoconjugate administration.

The compositions of the present invention are administered in single or multiple doses and may be injected parenterally, i.e., intravenously, intraparitoneally, or the like. Thus the invention provides compositions for parenteral administration which comprise a solution of pyrogen free glycoprotein or synthetic ligand dissolved in an aqueous carrier. A variety of carriers can be used, e.g., water, buffered water. 0.9% saline. 0.3% glycine, or the like. These solutions are sterile and generally free of particulate matter. These compositions may be sterilized by conventional, well known filtration sterilization techniques. The compositions may contain pharmaceutically acceptable auxiliary substances as required to approximate physiological conditions such as pH adjusting and buffering agents, toxicity adjusting agents, or the like, for example, sodium acetate, sodium chloride, potassium chloride, calcium chloride, sodium lactate, etc.

Kits may be supplied including the present compositions. these kits may include immunoconjugates and instructions for use.

The following examples are offered by way of illustration and not limitation:

EXPERIMENTAL

EXAMPLE I

Experimental Preparations

All studies were carried out in 7–8 week old Balb/c mice (Bantin and Kingman, Hull, U.K.). Mice were housed in plastic cages on sawdust bedding with standard laboratory diet and water containing 0.1% w/v sodium iodide ad libitum.

1. XMMCO-791-RTA Immunotoxin.

The preparation of XMMCO-791-RTA conjugates is disclosed in U.S. application Ser. No. 06/896,999, now abandoned which is hereby incorporated by reference. Essentially, monoclonal antibody XMMCO-791 (isotype IgG2b) was produced in ascites form following intraperitoneal inoculation of XMMCO-791 hybridoma cells (A.T.C.C. Accession No. HB 9173) into Balb/c mice. Ascites fluid was fractionated by Sepharose-protein A chromatography to yield an IgG2b fraction.

RTA conjugates were prepared by coupling ricin toxin A chain to antibody via a disulfide linkage. Briefly, XMMCO-791 antibody was reacted with N-succinimidyl-3-(2-pyridydithio)proprionate (SPDP). Excess reactant was removed by dialysis and the modified antibody coupled with RTA (Embleton et al., *Cancer Research* (1986)46:5524–28). Conjugates were purified by Sephadex G150 chromatography.

2. Radiolabelled Preparations.

Monoclonal antibody XMMCO-791 was labelled with $^{131}I$ or $^{125}I$, as disclosed in U.S. application Ser. No. 06/875,256, now U.S. Pat. No. 4708862 which is hereby incorporated by reference, to a specific activity of 1 millicurie/mg using Iodogen as the oxidizing agent and with unreacted radioiodine removed by gel filtration on Sephadex G-25.

a. Immunoaffinity purified $^{125}I$-Ricin A Chain ($^{125}I$[RTA]).

RTA was radiolabelled with $^{125}I$ to a specific activity of 0.5 millicuries/mg using Iodogen as the oxidizing agent and free $^{125}I$ removed by gel filtration on Sephadex G-25.

b. $^{125}I$-labelled XMMCO-791-RTA conjugates ($^{125}I$-[XMMCO-791-RTA]).

XMMCO-791-RTA conjugates were wholly radiolabelled with $^{125}I$ to a specific activity of 1 millicurie/mg using Iodogen. Free $^{125}I$ was removed by gel filtration on Sephadex G-25 to yield conjugates in which RTA and antibody component were radioiodine labelled.

c. $^{125}I$-labelled RTA conjugated to XMMCO-791 antibody ($^{125}I$-[RTA]-XMMCO-791)

Conjugates were prepared in which $^{125}I$-labelled RTA was coupled to antibody XMMCO-791. Briefly, RTA was allowed to react with a 10-fold molar excess of 2-2-dithiodipyridine to block and protect the free sulfhydryl group for oxidation. The radioiodination was conducted by reacting the sulfhydryl-protected RTA with $^{125}I$-sodium iodide at 1.0 to 1.5 mCi/mg RTA using Iodogen at 0.1 mg/ml protein. Excess unreacted iodide was removed and the protecting group was removed by reaction with 50 mM dithiothreitol for 1 to 2 hours at room temperature. The resulting $^{125}I$-RTA-SH was concentrated to 2.5 to 5.0 mg/ml and conjugated to monoclonal antibody XMMCO-791 (specific activities 0.26 and 0.35 millicuries/mg protein).

d. $^{131}I$-labelled RTA conjugated to XMMCO-791 antibody ($^{131}I$-[RTA]-XMMCO-791).

Conjugates were prepared also by the above method in which $^{131}I$-labelled RTA was coupled to XMMCO-791 (specific activity $9.7\times10^4$ counts/min/μg protein).

e. $^{125}I$-labelled RTA conjugated to $^{131}I$-labelled XMMCO-791 antibody ($^{125}I$-[RTA]-$^{131}I$-[XMMCO-791]).

A conjugate was prepared in which $^{125}I$-labelled RTA was linked to 131I-labelled XMMCO-791 antibody using the above general procedures.

EXAMPLE II

Analytical Techniques

1. Blood Survival and Biodistribution of Radiolabelled Monoclonal Antibody XMMCO-791 and Immunotoxin.

Groups of Balb/c mice were injected intravenously under ether anaesthesia with 0.2 ml of preparations diluted in PBS to contain $10^6$–$10^7$ cpm of radioiodine. Blood samples (10 μl) were collected at intervals between 5 minutes and 24 hours from the tail vein into microcapillary pipettes. $^{125}I$ and/or $^{131}I$ in aliquots of injected materials and in the blood samples were counted in a two channel LKB 80,000 well gamma counter. Blood levels of radiolabel were calculated with respect to immediately post injection count which was calculated from the count rate in the injected material and the blood volume (ml) of individual mice taken as 11.2% of the body weight (g) (Pimm et al., *Eur. J. Cancer Clin. Oncol.* (1987) 23:521–527.

In some cases the mice were-killed by cervical dislocation at timed intervals and organs and carcass were weighed and their radioactivity determined in a gamma counter. Tissue levels of radiolabel were expressed as the % injected dose present in whole organs and per gram of tissue.

2. Determination of Whole Body Retention of Radiolabelled RTA Preparations.

Groups of 2–4 Balb/c mice were injected intraperitoneally with 0.2 ml of preparations diluted in PBS to contain approximately $10^5$ cpm of radioiodine. Radioactivity in individual mice was counted immediately and then at daily intervals in a 7.5 cm×7.5 cm well scintillation crystal detector (John Caunt Scientific, Oxford, U.K.). Count rates were corrected for physical decay and background counts and expressed as a percentage of the initial whole body count rate.

3. Sephacryl S-300 Gel Filtration of Serum.

Samples of radiolabelled preparations added to normal mouse serum, or serum preparations from blood taken by cardiac puncture from treated mice, were examined by gel filtration chromatography. One milliliter of preparation was passed through a 90 cm×1.5 cm column of Sephacryl S-300 (Pharmacia, Uppsala, Sweden) in PBS at a flow rate of 15 ml/hr with absorption of ultraviolet light at 280 nm monitored continuously on the eluate, and 2 ml fractions collected for radioactivity counting.

4. Immunoprecipitation of Serum Borne Radioiodine-Labelled Products.

In order to determine the proportion of serum-borne radiolabel attached to protein and immunoglobulin. 200 μl of either rabbit anti-mouse immunoglobulin antiserum or 10% trichloracetic acid was added to 20 μg of serum from mice injected intravenously with radiolabelled preparations. With the original starting radiolabelled preparations aliquots were added to 20 μl of carrier normal mouse serum before addition of rabbit antiserum or TCA. The mixtures were incubated overnight at 4° C. and protein precipitates sedimented by centrifugation. 110 μl aliquots of supernatant were withdrawn from each tube and counted for radioactivity along with the pellet and remaining supernatants. The precipitated counts was calculated as:

$$\frac{\text{cpm } 110\ \mu\text{l supernatant} + \text{pellet} - \text{cpm } 110\ \mu\text{l supernatant}}{\text{cpm in pellet} + 110\ \mu\text{l supernatant} + \text{cpm in } 110\ \mu\text{l supernatant}}$$

Treated mice were killed at intervals and blood and tissue levels of radioactivity determined. Tissue levels of radiolabel were expressed as the % of injected dose whole organ and per gram of tissue and as a tissue to blood ratio calculated as:

$$\frac{\text{Count rate of radioiodine/gram tissue}}{\text{Count rate of radioiodine/gram blood}} \times 100$$

EXAMPLE III

Biodistribution

1. Comparison of the Blood Survival of XMMCO-791-RTA Immunotoxin with XMMCO-791 Antibody and Ricin A Chain.

The blood survival pattern of XMMCO-791-RTA immunotoxin containing $^{125}$ RTA ($^{125}$I-[RTA]-XMMCO-791) in normal Balb/c mice demonstrated a rapid initial elimination so that 15 minutes after injection, an average of only 32.5 percent of the injected dose of radioactivity was present in blood (T ½ α 9.0 mins). Blood levels of $^{125}$I showed a subsequent small rise and then radioactivity was more slowly eliminated, decreasing from 22 percent at 2 hours to 4.3 percent at 24 hours (T ½ B 9.8 hrs.) This blood survival pattern is very similar to that observed with unconjugated $^{125}$I-RTA, which was also initially rapidly eliminated (T ½ α 6.7 mins). An increase in blood $^{125}$I levels between 15 and 30 minutes after injection was also clearly established. In comparison $^{131}$I labelled XMMCO-791 antibody showed a much longer survival in blood so that at 20 minutes, serum $^{131}$I levels were 60–70% of the initial (immediate post injection) level. At 24 hours, serum levels were still 27% of the initial values. These results indicate that the elimination of XMMCO-791-RTA from blood is largely dictated by the RTA component. This is further supported by analysis of the blood survival of XMMCO-791-RTA in which both components are labelled with $^{125}$I ($^{125}$I-[XMMCO-791-RTA]), since there was again a rapid elimination of serum $^{125}$I. This was more precisely demonstrated by analysis of the elimination of a conjugate in which the RTA and antibody moieties carried different radiolabels ($^{125}$I-[RTA]-$^{131}$I-[XMMCO-791]). Blood levels of $^{125}$I, as a measure of RTA rapidly decreased, only 15% being present after 18 minutes. The remaining $^{125}$I labelled product was then eliminated more slowly; levels of 3% remaining after 7 hours. Comparably, there was a rapid clearance of $^{131}$I, only 22% being detected after 18 minutes. This was followed by a less rapid elimination of the blood $^{131}$I product.

2. Organ Distribution of $^{131}$I-[RTA]-XMMCO-791.

Organ distribution studies of $^{131}$I following injection of $^{131}$I-[RTA]-XMMCO-791 demonstrated a rapid uptake into liver. Within 2 minutes of injection 37 percent of the injected dose was localized in the liver and peak levels of 40 percent of the injected dose were observed after 10 minutes. Thereafter liver $^{131}$I radioactivity progressively declined with 7 percent of the injected dose remaining after 120 minutes. This rapid uptake into liver is further emphasized when radioactivity/g tissue is compared. In comparison, only low levels of $^{131}$I were localized in kidney, spleen, lung and heart although the intestinal levels rose after 10 minutes, probably representing metabolised conjugate products.

3. Whole Body Survival of XMMCO-791-RTA.

The whole body survival of $^{125}$I-[RTA]-XMMCO-791 and $^{125}$I-[RTA] shows that the RTA-containing fractions are rapidly eliminated, so that less than 10% of the injected dose survives 20 hours. This contrasts with the longer body survival of $^{131}$I-[XMMCO-791] where more than 50% survives 20 hours. Again, this rapid elimination of the RTA moiety was further demonstrated in tests using $^{125}$I-[RTA]-$^{131}$I-[XMMCO-791].

4. Nature of $^{125}$I-labelled Product in Blood Following Injection of $^{125}$I-[RTA]-XMMCO-791.

In order to determine whether circulating $^{125}$I in mice injected with $^{125}$I-[RTA]-XMMCO-791 was bound to XMMCO-791 antibody, serum was analyzed for $^{125}$I precipitable with rabbit anti-mouse IgG antiserum (RA IgG) and this was compared with the total protein (TCA precipitable) radioactivity. Almost all (82 to 98%) of the $^{125}$I was precipitable by rabbit IgG and TCA from serum taken 5 minutes following conjugate injection. After 30 minutes, however, only 50 to 60 percent of serum borne $^{125}$I was precipitable in protein bound form. (The non-protein bound radioactivity is probably free $^{125}$I produced following hepatic metabolism of conjugate which peaks in the liver 10 minutes after injection.)

5. Characteristics of Circulating XMMCO-791-RTA Conjugate.

A Sephacryl S300 gel filtrate of normal mouse serum to which was added $^{125}$I-[XMMCO-791-RTA] and $^{131}$I-[XMMCO-791] demonstrated that the immunotoxin component was clearly distinguishable from free antibody. Serum from mice 5, 30 and 120 minutes after intravenous injection of a mixture of $^{125}$I-[XMMCO-791-RTA] and $^{131}$I-[XMMCO-791] antibody showed a progressive decrease in molecular size of the circulating $^{125}$I labelled product. After 120 minutes, the $^{125}$I peak was coincident with that of the $^{131}$I labelled antibody. In this test both the RTA and antibody components of the immunotoxin had been labelled with $^{125}$I, so that it was not possible to identify the nature of the $^{125}$I labelled product in serum. This was more precisely investigated by analyzing the survival of radiolabelled products in serum following injection of a conjugate in which only the RTA was labelled ($^{125}$I-[RTA]-XMMCO-791). Sephacryl S300 chromatography of this conjugate in normal mouse serum demonstrated a major component together with a shoulder to the descending peak. The product remaining in serum 5 minutes after intravenous injection had a similar chromatographic profile although the peak of low molecular weight material was significantly increased. There was also a third peak of smaller molecular weight product (possibly free RTA). Chromatographic profiles of $^{125}$I in serum taken 30 minutes after injection showed a more dramatic change with radiolabel being associated with the lower molecular weight material. Finally, by 2 hours the product in serum was contained predominantly in a single peak which represents product(s) only slightly larger than XMMCO-791 antibody.

EXAMPLE IV

Biodistribution Modification

1. Modification of Biodistribution of XMMCO-791-RTA Immunotoxin.

Ricin toxin A chain uptake into liver in rodents is mediated through its reaction with a receptor on hepatic Kupffer cells. This is thought to involve recognition of mannose on the oligosaccharide chains of the toxin. Based upon these considerations experiments were carried out to determine the effectiveness of glycoproteins and related products in blocking hepatic uptake of the immunotoxin.

Mice were injected intravenously with radioiodine labelled immunotoxin or free RTA together with agents designed to modify hepatic uptake. These agents were ovalbumin (from chicken egg, Sigma, Grade V, crystallized, Sigma Chemical Co. Ltd., Dorset, U.K.), ovomucoid (from chicken egg white, Sigma Trypsin inhibitor, type 111-0), mannan (from Saccharomyces cerevisiae, Sigma), Fettemulsion (soya bean oil emulsion in water stabilized by egg yolk phosphatides and glycerol), and mannosyl$_3$lysine$_2$ (Man$_3$Ly$_2$), a synthetic ligand for mannose receptors on macrophages which is disclosed in U.S. Pat. No. 4,386,026.

2. Modification of Biodistribition of XMMCO-791-RTA By Glycoproteins.

Ovalbumin administered intravenously together with XMMCO-791-RTA ($^{125}$I-[XMMCO-791-RTA]) very effectively increased blood survival of radioactive product. the blood half-life of immunotoxin being prolonged from 4 minutes to 20 minutes. Organ distribution studies of XMMCO-791-RTA indicate that maximum liver uptake occurs 10 min. after immunotoxin administration. For comparative studies, therefore, the influence of liver blocking on immunotoxin was evaluated by determining the organ and blood levels of radioactivity 10 minutes after administration and this is expressed as a tissue to blood ratio (Table 1). XMMCO-791-RTA immunotoxin in which both the RTA and antibody moieties are labelled with $^{125}$I is preferentially localized in liver, the liver to blood ratio being 5.1:1. Liver uptake of immunotoxin was markedly reduced when injected together with ovalbumin (doses 10 or 20 mg/mouse), the liver to blood ratio of radioactivity being reduced to 1.6:1 and 1.2:1 respectively. The only other organ where ovalbumin modified immunotoxin was in the spleen. Liver uptake of $^{125}$I-[RTA] was similarly inhibited by administration of ovalbumin (10 or 20 mg), the liver to blood ratio being reduced from 6.9:1 to 1.8:1 and 1.2:1 respectively. In comparison, monoclonal antibody XMMCO-791 shows no propensity for liver localization (Table 1) indicating the important influence of the RTA moiety on the biodistribution of immunotoxin. This was further investigated using XMMCO-791-RTA immunotoxin in which only the RTA component was $^{125}$I-labelled ($^{125}$I-[RTA]-XMMCO-791). Ovalbumin again proved to be highly effective for limiting hepatic uptake of immunotoxin and comparable effects were produced by ovomucoid and mannan (Table 2). Fettemulsion, a non-specific reticuloendothelial system (RES) blocking agent, had no effect on hepatic uptake of XMMCO-791-RTA further supporting the view that hepatic uptake of RTA immunotoxins involves binding to specific receptors.

A time course investigation of the effect of ovalbumin (20 mg/mouse) injected together with $^{125}$I-[XMMCO-791-RTA] was performed indicating that ovalbumin treatment led to elevated blood levels of immunotoxin over the first 60 minutes. Thereafter the blood levels in control and ovalbumin-treated mice were similar. Analysis of liver uptake indicated that this occurred rapidly (10 minutes) in control mice and then liver levels decayed probably due to metabolic degradation. In ovalbumin treated mice the intial uptake was lower, but remained constant for up to 30 minutes and then decayed more slowly. (This probably reflects the transient blocking effect by ovalbumin of liver RES cells.)

TABLE 1

BIODISTRIBUTION IN MICE OF RADIOLABELLED ANTIBODY, RICIN A CHAIN AND IMMUNOTOXIN: EFFECT OF OVALBUMIN

| Expt. No. | Radiolabelled Preparation | Dose ovalbumin (mg)[1] | Tissue to blood ratio of $^{125}$I in[2]: Liver | Kidney | Spleen | Intestine | Heart | Lung | Carcass |
|---|---|---|---|---|---|---|---|---|---|
| 1 | $^{125}$I-791T/36 | — | 0.4 | 0.2 | 0.3 | 0.004 | 0.2 | 0.8 | 0.8 |
| 3 | $^{125}$I-RTA | — | 6.9 | 6.6 | 1.7 | 0.8 | 0.6 | 0.8 | 1.4 |
| | | 10 | 1.8 | 5.5 | 0.6 | 0.1 | 0.4 | 0.6 | 0.6 |
| | | 20 | 1.2 | 4.2 | 0.4 | 0.1 | 0.4 | 0.4 | 0.8 |
| 2 | $^{125}$I-[791T/36-RTA] | — | 5.1 | 0.4 | 1.8 | 0.1 | 0.4 | 0.7 | 0.5 |
| | | 10 | 1.6 | 0.4 | 0.5 | 0.04 | 0.8 | 1.1 | 0.6 |
| | | 20 | 1.2 | 0.8 | 0.4 | 0.05 | 0.8 | 0.5 | 0.4 |

[1]Injected intravenously together with radiolabelled preparation

[2]Ten minutes after injection. Mean of two mice.

TABLE 2

INFLUENCE OF BLOCKING AGENTS ON BIODISTRIBUTION OF [$^{125}$I-RTA]-791T/36 IMMUNOTOXIN IN MICE

| Expt. No. | Blocking Agent [1] | Dose | Tissue:Blood Ratio of $^{125}$I in: [2] Liver | Kidney | Spleen | Intestine | Heart | Lung | Carcass |
|---|---|---|---|---|---|---|---|---|---|
| 1 | — | — | 4.6 | 1.0 | 1.1 | 0.1 | 0.4 | 1.0 | 1.0 |
| | Ovalbumin | 20 mg | 1.6 | 0.9 | 0.6 | 0.1 | 0.3 | 0.8 | 0.8 |
| | Ovomucoid | 5 mg | 1.3 | 0.8 | 0.5 | 0.1 | 0.3 | 2.6 | 0.8 |
| 2 | — | — | 4.6 | 0.8 | 0.8 | 0.1 | 0.3 | 1.9 | 0.7 |
| | Ovomucoid | 10 mg | 1.4 | 0.3 | 0.3 | 0.05 | 0.3 | 0.7 | 0.6 |
| | Mannan | 8 mg | 1.8 | 1.1 | 0.4 | 0.2 | 0.5 | 1.1 | 1.0 |
| 3 | — | — | 4.9 | 0.8 | 0.9 | 0.1 | 0.3 | 1.4 | 0.3 |
| | Ovalbumin | 20 | 1.0 | 0.6 | 0.3 | 0.04 | 0.3 | 0.6 | 0.3 |
| | Fettemulsion | 0.2 ml | 4.6 | 0.7 | 1.0 | 0.05 | 0.3 | 0.8 | 0.3 |
| 4 | — | — | 4.6 | 1.0 | 1.1 | 0.3 | 0.3 | 1.6 | 0.5 |
| | Ovalbumin | 20 mg | 1.6 | 0.9 | 0.6 | 0.1 | 0.2 | 1.0 | 0.4 |
| | Man3Ly2 | 2 mg | 1.3 | 0.8 | 0.3 | 0.1 | 0.2 | 1.2 | 0.4 |
| 5 | — | — | 3.5 | 0.9 | 1.7 | 0.08 | 0.2 | 0.9 | 0.4 |
| | Ovalbumin | 20 mg | 1.3 | 1.0 | 0.5 | 0.06 | 0.2 | 0.6 | 0.3 |
| | Man3Ly2 | 2 mg | 1.4 | 1.1 | 0.8 | 0.07 | 0.3 | 1.8 | 0.4 |

[1]Injected intravenously together with radiolabelled immunnotoxin

3. Characterization of Circulating RTA-XMMCO-791 in Ovalbumin Treated Mice.

When serum from mice injected with $^{125}$I-[XMMCO-791-RTA] was analyzed by Sephacryl S-300 gel filtration chromatography it was seen that the change in its molecular profile was less rapid when immunotoxin was injected together with ovalbumin. Thus the higher molecular weight immunotoxin components were still present one hour post-injection in the presence of ovalbumin whereas in control mice only lower molecular weight material (probably representing conjugate of RTA:antibody molar ratio of 1:1) persisted.

4. Modification of Biodistribution of XMMCO-791-RTA By Mannosyl-lysine.

Mannosyl-lysine (Man$_3$Ly$_2$), a reagent designed specifically to be taken up by mannose receptors in coated pit regions of hepatic kupffer cells proved to be highly effective for limiting hepatic uptake of immunotoxin (Table 2 expts. 4 and 5) with doses of 2 mg Man$_3$Ly$_2$/-mouse producing a 2 to 3 fold reduction in the liver to blood ratio.

The present invention provides methods and compositions for the enhancement of the biodistribution of immunoconjugates. It is believed that the compositions block receptors in tissues responsible for the elimination of waste and the filtration of blood, particularly in the liver.

Although the present invention has been described in some detail for purposes of clarity and understanding, it will be obvious to those skilled in the art that certain changes and modifications may be practiced within the scope of the appended claims.

What is claimed is:

1. A method for enhancing the bioavailability of an immunotoxin, said method comprising administering said immunotoxin to a mammalian host concomitantly with the administration of a blocking agent selected from compounds of the formula:

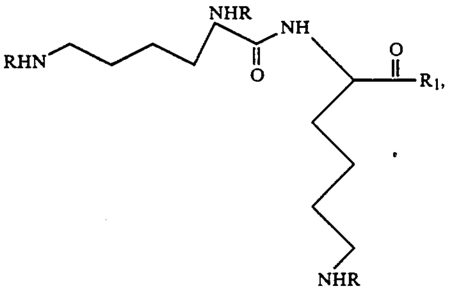

wherein R is a saccharide compound selected from the group consisting of

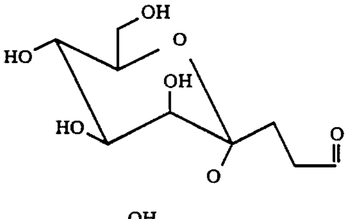

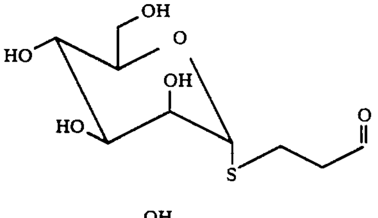

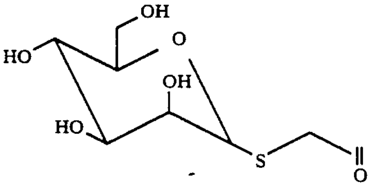

-continued

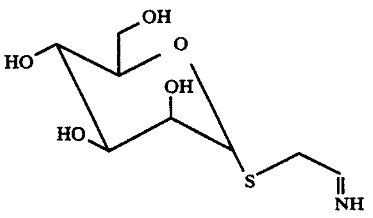

and $R_1$ is selected from the group consisting of hydroxyl and $NHR_2$ wherein $R_2$ is 6-aminohexyl or acid addition salts. thereof.

2. A method according to claim 1, wherein said blocking agent is capable of binding to Kuppfer cells.

3. A method according to claim 1, wherein said blocking agent is mannosyl$_3$lysine$_2$.

4. A method according to claim 1, wherein said immunotoxin contains the A chain of ricin or a subunit thereof.

5. A method according to claim 4, wherein said immunotoxin is selected from the group consisting of XMMME-001-RTA, XMMME-002-RTA, XMMCO-791-RTA, XMMCO-228-RTA, XMMLY-H65-RTA, and XMMLY-4A2.

6. A method according to claim 1, wherein the dose of said blocking agent is in the range of about 0.1 mg/kg to about 1.0 g/kg of host body weight.

7. A method according to claim 6, wherein the blood concentration of immunoconjugate is increased in the range of about 1.1:1 to 10:1.

8. An immunoconjugate composition comprising an immunotoxin and a blocking agent selected from compounds of the formula:

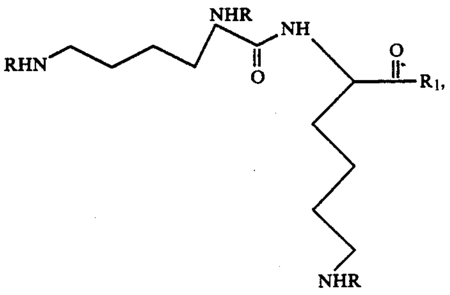

wherein R is a saccharide compound selected from the group consisting of

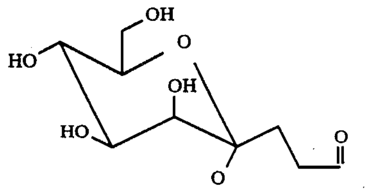

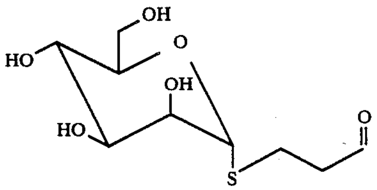

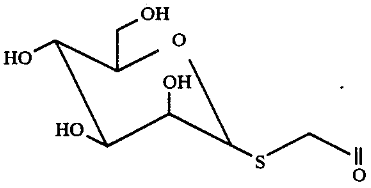

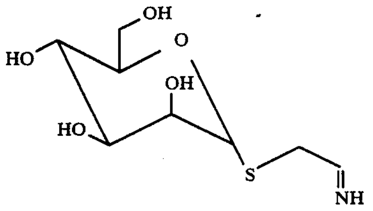

and $R_1$ is selected from the group consisting of hydroxyl and $NHR_2$ wherein $R_2$ is 6-aminohexyl or acid addition salts thereof.

9. An immunoconjugate composition according to claim 8, wherein said immunoconjugate and said blocking agent are in an aqueous mixture.

10. A kit for the administration of an immunotoxin comprising an immunoconjugate composition according to claim 8, a blocking agent, and instructions for use.

* * * * *